United States Patent
Yang et al.

(10) Patent No.: US 8,647,608 B2
(45) Date of Patent: *Feb. 11, 2014

(54) THERAPEUTIC DENTAL COMPOSITION AND RELATED METHODS

(71) Applicant: 3M Innovative Properties Company, St. Paul, MN (US)

(72) Inventors: Jie Yang, Woodbury, MN (US); Bhaskar V. Velamakanni, Woodbury, MN (US); Sumita B. Mitra, West St. Paul, MN (US); Alphonsus V. Pocius, Maplewood, MN (US); John J. Stofko, Jr., St. Paul, MN (US); Jeremy M. Yarwood, Maplewood, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/664,452

(22) Filed: Oct. 31, 2012

(65) Prior Publication Data

US 2013/0052146 A1 Feb. 28, 2013

Related U.S. Application Data

(63) Continuation of application No. 12/594,994, filed as application No. PCT/US2008/069651 on Jul. 10, 2008.

(60) Provisional application No. 60/951,761, filed on Jul. 25, 2007.

(51) Int. Cl.

| | | |
|---|---|---|
| A61K 8/41 | (2006.01) | |
| A61K 8/42 | (2006.01) | |
| A61K 8/85 | (2006.01) | |
| A61K 8/87 | (2006.01) | |
| A61K 8/89 | (2006.01) | |
| A61Q 11/00 | (2006.01) | |
| C07C 215/10 | (2006.01) | |
| C07C 233/18 | (2006.01) | |

(52) U.S. Cl.
USPC ............... 424/54; 424/52; 514/42; 536/29.1; 554/66; 564/507

(58) Field of Classification Search
None
See application file for complete search history.

(56) References Cited

U.S. PATENT DOCUMENTS

| | | |
|---|---|---|
| 4,871,786 A | 10/1989 | Aasen |
| 5,130,347 A | 7/1992 | Mitra |
| 5,362,480 A | 11/1994 | Au |
| 5,438,076 A | 8/1995 | Friedman |
| 5,468,477 A | 11/1995 | Kumar |
| 5,525,330 A * | 6/1996 | Gaffar et al. ............... 424/52 |
| 5,525,648 A | 6/1996 | Aasen |
| 5,607,663 A | 3/1997 | Rozzi |
| 5,616,746 A | 4/1997 | Mahieu |
| 5,624,906 A | 4/1997 | Vermeer |
| 5,662,887 A | 9/1997 | Rozzi |
| 5,725,882 A | 3/1998 | Kumar |
| 5,866,630 A | 2/1999 | Mitra |
| 5,871,714 A | 2/1999 | Budny |
| 5,876,208 A | 3/1999 | Mitra |
| 5,888,491 A | 3/1999 | Mitra |
| 6,312,668 B2 | 11/2001 | Mitra |
| 6,316,029 B1 | 11/2001 | Jain |
| 6,620,405 B2 | 9/2003 | Oxman |
| 7,223,826 B2 | 5/2007 | Ali |
| 2002/0136768 A1 | 9/2002 | Staats |
| 2003/0099602 A1 | 5/2003 | Levin |
| 2003/0108611 A1 | 6/2003 | Bosch |
| 2003/0114553 A1 | 6/2003 | Karim |
| 2003/0129144 A1 | 7/2003 | Scott |
| 2003/0175367 A1 * | 9/2003 | Mao ............................ 424/725 |
| 2004/0147595 A1 | 7/2004 | Kjelleberg |
| 2004/0151691 A1 | 8/2004 | Oxman |
| 2004/0185013 A1 | 9/2004 | Burgio |
| 2005/0058744 A1 | 3/2005 | Steinberg |
| 2005/0265948 A1 | 12/2005 | Ridley |
| 2005/0281773 A1 | 12/2005 | Wieland |
| 2005/0282261 A1 | 12/2005 | Sauter |
| 2006/0134239 A1 | 6/2006 | Weide |
| 2008/0312395 A1 | 12/2008 | Muller |
| 2009/0304799 A1 | 12/2009 | Baker, Jr. |
| 2009/0305196 A1 | 12/2009 | Karim |
| 2010/0150847 A1 | 6/2010 | Yang |
| 2010/0330013 A1 | 12/2010 | O'Connell |

FOREIGN PATENT DOCUMENTS

| | | |
|---|---|---|
| DE | 4406745 | 9/1995 |
| DE | 4406746 | 9/1995 |
| EP | 0 057 323 | 5/1983 |
| EP | 0945119 | 9/1999 |

(Continued)

OTHER PUBLICATIONS

Burt S. Essential oils: their antibacterial properties and potential applications in foods—a review. International Journal of Food Microbiology 94 (2004) 223-253.*

(Continued)

*Primary Examiner* — Frederick Krass
*Assistant Examiner* — Michael P Cohen
(74) *Attorney, Agent, or Firm* — Nicole J. Einerson

(57) ABSTRACT

Dental compositions are provided comprising a compound of Formula I or a pharmaceutically acceptable salt thereof:

I

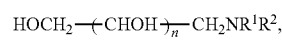

wherein n is an integer from about 2 to about 5.

21 Claims, No Drawings

(56) References Cited

FOREIGN PATENT DOCUMENTS

| JP | 55069506 | 5/1980 |
|---|---|---|
| JP | 2-107969 | 4/1990 |
| JP | 09-509665 | 9/1997 |
| JP | 09-509666 | 9/1997 |
| JP | 11-228989 | 8/1999 |
| JP | 2005-029484 | 3/2005 |
| WO | WO 90/04789 | 3/1990 |
| WO | WO 94/24097 | 10/1994 |
| WO | WO 95/23583 | 9/1995 |
| WO | WO 9523582 A1 * | 9/1995 |
| WO | WO 02/30380 | 4/2002 |
| WO | WO 2006/029893 | 3/2006 |
| WO | WO 2007/054203 | 5/2007 |
| WO | WO 2007/079069 | 7/2007 |
| WO | WO 2008/033911 | 3/2008 |
| WO | WO 2009/014905 | 1/2009 |

OTHER PUBLICATIONS

International Search Report PCT/US2008/069651.
Homer KA et al., Effects of N-acetylglucosamine on carbohydrate germentation by *Streptococcus* mutans NCTC 10449 and *Streptococcus sobrinus* SL-1, Infect Immun. Jan. 1993, vol. 61, No. 1, pp. 295-302.
A.F. Paes Leme, H. Koo, C.M. Bellato, G. Bedi, and J.A. Cury (2006), The Role of Sucrose in Cariogenic Dental Biofilm Formation—New Insight, J. Dent. Res., 85(10), 878-887.
M. Fontana, and D.T. Zero (2006), Assessing Patients' Caries Risk, JADA, 137(9), 1231-1239.
M. Marotta, A. Martino, A. De Rosa, E. Farina, M. Carteni, M. De Rosa (2002), Degradation of dental plaque glucans and prevention of glucan formation using commercial enzymes, Process Biochemistry, 38, 101-108.
M. Inoue, T. Yakushiji, M. Katsuki, N. Kudo and T. Koga (1988), Reduction of the adherence of *Streptococcus sobrinus* insoluble α-D-glucans by endo-(1,3)-α-D-glucanase. Carbohydrate Research, 182, 277-286.
D. Kim, R. Su-jin, H. Soo-jin, K. Do-won and K.J. Ho-sang (1999), Characterization of a novel carbohydrase from *Lipomyces starkeyi* KSM22 for dental application. Microbiol Biotechnol, 9(3), 260-264.
C.F. Schechtele, R.H. Staat and S.K. Harlander (1975), Dextranases from oral bacteria: inhibition of water-insoluble glucan production and adherence to smooth surfaces by *Strptococcus* mutans. Infect Immun. 12(2), 309-317.
S. Hamada, J. Mizuno, Y. Murayama, T. Ooshima and N. Masuda, S. Sobue (1975), Effect of dextranase on the extracellular polysaccharide synthesis of *Streptococcus mutans*: Chemical and Scanning Electron Microscopy SStudies, Infect Immun, 12(6), 1415-1425.
P.E. Kolenbrander and R.N. Andersen (1989), Infect. Immun., Inhibition of Coaggregation between *Fusobacterium nucleatum* and *Porphyromonas* (Bacteroides) *gingivalis* by Lactose and Related Sugars; 57, 3204-3209.
B. Shaniztki, D. Hurwitz, N. Smorodinsky, N. Ganeshkumar and E.I. Weiss (1997), Infect. Immun. Identification of a *Fusobacterium nucleatum* PK1594 Galactose-Binding Adhesin Which Mediates Coaggregation with Periopathogenic Bacteria and Hemagglutination; 65, 5231-5237.
R.J. Gibbons, J.V. Qureshi (1979), Infection and Immunity, Inhibition of Adsorption of *Streptococcus mutans* Strains toSaliva-Treated. Hydroxyapatite by Galactose and Certain Amines; 26(3), 1214-1217.
Oral Health in America: A Report of the Surgeon General, Executive Summary (2000), Rockville, MD; U.S. Natl. Inst. Of Dental and Craniofacial Research, 332 pages.
S. Imazato, M. Torii, Y. Tscuchitani, J.F. McCabe, and R.R.B. Russell (1994), Incorporation of Bacterial Inhibitor into Resin Composite, J. Dent. Res.; 73(8); 1437-1443.
Crane et al., "Isonucleosides from Glucosamine", Journal of Carbohydrates Nucleosides, 7(5), 281-296 (1980).
MSDS for Carbomer 910, 934, 934p, 940, 941, downloaded from the internet on Feb. 12, 2012, <http://www.sciencelab.com/msds.php?msdsID=9925741> 5 pgs.
Bakri et al., "Inhibitory effect of garlic extract on oral bacteria", Archives of Oral Biology (2005) 50, 645-651.
Park et al, "Characteristics of Different Molecular Weight Chitosan Films Affected by the Type of Organic Solvents", Journal of Food Science, vol. 67, Nr. 1, (2002) 194-197.
Rudnic et al., "Oral Solid Dosage Forms", Chapter 89 is Remington's Pharmaceutical Sciences, 18th Edition, Gennaro et al. (eds.) Mack Publishing Co., Easton, PA, 1990.
J. Thomas et al., "The Effect of Glucose Derivatives on *Streptococcus mutans* Plaque Production In Vitro", FEMS Microbilolgy Letters 4 (1978) 27-30.
Supplementary European Search Report (EP App. No. 08 79 6139) Aug. 10, 2012, 3 pages.

\* cited by examiner

THERAPEUTIC DENTAL COMPOSITION AND RELATED METHODS

TECHNICAL FIELD

The present disclosure relates to dental compositions, and more specifically, to dental compositions and methods to inhibit biofilm formation in the oral cavity of a subject.

BACKGROUND

Dental plaque, which may include bacteria such as *Streptococcus mutans*, comprises a biofilm that forms on surfaces in the oral cavity. Dental plaque is at least partly responsible for dental caries, gingivitis, and periodontal diseases. Bacteria in dental plaque metabolize carbohydrates (for example, simple sugars) in the mouth and produce acids that can etch tooth enamel. The dentin thus exposed can then be colonized by bacteria. Dental plaque can serve as a substrate for the deposition of tartar or calculus. Build up of calculus can lead to gingivitis and, ultimately, to periodontal disease. A currently available method to remove dental plaque from teeth is mechanical removal with, for example, dental floss or a toothbrush. A toothbrush can aid in removing dental plaque from exposed surfaces of a tooth, and dental floss can aid in removing dental plaque from, for example, interproximal and subgingival surfaces. Proper and regular use of dental floss and a toothbrush can mechanically remove or reduce dental plaque, and can reduce the incidence of dental caries, gingivitis, and periodontal disease. Certain antimicrobial formulations are available (in the form of mouthwashes, rinses, and toothpastes, for example) to aid in the control and treatment of dental plaque, dental caries, gingivitis, and periodontal disease.

SUMMARY

As noted above, proper and regular use of dental floss and a toothbrush can reduce dental plaque and the incidence of dental caries. However, dental floss and a toothbrush are not always used properly and regularly. Moreover, a biofilm matrix such as dental plaque may contribute to the isolation of bacteria from the protective effect of antimicrobial compounds and, thus, may interfere with the function of antimicrobial formulations such as mouthwashes, rinses, and toothpastes. As a result, alternative methods to control or prevent dental plaque, rather than to remove it, are desirable. Thus, we recognize that there is a need for compositions and methods to inhibit the formation of biofilms, particularly in the oral cavity.

In one aspect, the invention provides a dental composition comprising a compound of Formula I or a pharmaceutically acceptable salt thereof:

$$\text{HOCH}_2\!-\!(\text{CHOH})_n\!-\!\text{CH}_2\text{NR}^1\text{R}^2,\qquad\text{I}$$

wherein $R^1$ and $R^2$ are independently selected from a hydrogen atom, an alkyl group, $C(O)R^3$, and $SO_2R^4$; $R^3$ and $R^4$ are independently selected from an alkyl group, an aryl group, and an aralkyl group; and n is an integer from 2 to 5. In some embodiments, the pharmaceutically acceptable salt is free of unsubstituted or substituted tropolone. In some embodiments, $R^1$ and $R^2$ each comprise a hydrogen atom, or are independently selected from a hydrogen atom and an alkyl group. In certain embodiments, $R^1$ or $R^2$ independently comprise an alkyl group of about one to about ten carbon atoms. In other embodiments, $R^1$ comprises a hydrogen atom and $R^2$ comprises $C(O)R^3$ or $SO_2R^4$. Typically, $R^3$ comprises an alkyl group having from about one to about twenty-six carbon atoms, more typically from about six to about sixteen carbon atoms.

The dental composition of the invention may comprise a pharmaceutically acceptable salt having at least one counter ion selected from an inorganic anion, an organic anion, and combinations thereof. In certain embodiments, the counter ion is selected from fluoride, chloride, bromide, iodide, sulfate, tetraarylborate, tetrafluoroborate, carbonate, phosphate, acetate, benzoate, fumarate, maleate, tartrate, ascorbate, benzenesulfonate, toluenesulfonate, citrate, and combinations thereof.

The dental composition may further comprise a binder. The binder may comprise at least one addition polymer, at least one condensation polymer, or at least one addition polymer and one condensation polymer. In some embodiments, the binder comprises a film forming polymer. The polymer can be selected from the group consisting of an acrylic polymer, a vinyl polymer, an epoxy polymer, a polyurea, a polyester, a polyanhydride, a polysiloxane, a polyurethane, and/or combinations thereof. Typically, the polymer comprises an acrylic polymer.

In certain implementations of the invention, the dental composition may further comprise a pharmaceutically acceptable carrier such as ethanol. The dental composition may comprise a flavoring agent, a coloring agent, or both.

The dental composition may be a therapeutic dental composition. The dental composition is a biofilm inhibiting composition, i.e., it is useful for inhibiting the formation of biofilms. The composition is particularly useful for inhibiting the formation of dental plaque, and more particularly for inhibiting the formation of dental plaque in an oral cavity of a subject. The dental composition may be in a form of a solution, a dispersion, a suspension, an emulsion, a solid, a paste, a foam, or a gel.

In another aspect, the invention provides a method of inhibiting biofilm formation on a surface of the oral cavity of a subject, comprising the steps of (1) providing a composition comprising a compound of Formula I or a pharmaceutically acceptable salt thereof, and (2) applying the composition to a surface in the oral cavity of a subject. Typically, the subject is a human. The subject can be a non-human animal or mammal. The applying step may include immersing inserting, rinsing, spraying, brushing, swabbing, or combinations thereof. The method can include, in some embodiments, applying the composition to a hard surface (e.g., a tooth) in the oral cavity.

In yet another aspect, the invention provides a kit comprising (1) a composition comprising a compound of Formula I or a pharmaceutically acceptable salt thereof, and (2) an applicator. The applicator can be a container, a sprayer, a brush, a swab, a tray, or combinations thereof.

This summary is not intended to describe each and every embodiment or implementation of the present invention. Further embodiments, features, and advantages of the present invention will be apparent from the following detailed description thereof and from the claims.

DETAILED DESCRIPTION

In several places throughout the application, guidance is provided through lists of examples, which examples can be used in various combinations. In each instance, the recited list serves only as a representative group and should not be interpreted as an exclusive list.

As used herein,

The terms "comprises" and variations thereof do not have a limiting meaning where these terms appear in the description and claims;

Any recitation of numerical ranges by endpoints includes all numbers subsumed within that range (e.g., 1 to 5 includes 1, 1.5, 2, 2.75, 3, 3.80, 4, 5, etc.);

The terms "a," "an," "the," "at least one," and "one or more" are used interchangeably. Thus, for example, a composition that comprises "a" compound of Formula I can be interpreted to mean that the composition includes "one or more" compounds of Formula I;

The term "dental composition" refers to a composition for use in the oral cavity of a subject;

The term "binder" refers to a polymeric or oligomeric binder compound;

The term "film forming" refers to a property of a compound, binder, polymer, or composition wherein the compound, binder, polymer, or composition is in the form of a substantially continuous film when substantially free of solvent or carrier;

The term "therapeutic" refers to preventing, ameliorating, treating, improving, or curing a disease or condition;

The term "biofilm" refers to a matrix comprising bacteria;

The term "biofilm inhibiting" refers to limiting the formation or growth of a biofilm;

The term "acrylic polymer" refers to a polymer formed by polymerization or copolymerization of at least one ester of acrylic acid or methacrylic acid;

The term "hard surface" refers to a surface in the oral cavity comprising hard material, such as bone, dental enamel, dentin, and dental restorations; and The term "dental restorations" refers to fillings, inlays, onlays, veneers, temporary and permanent crowns or bridges, implants, or orthodontic devices such as brackets or archwires.

In one aspect, the dental composition of the invention comprises a compound of Formula I or a pharmaceutically acceptable salt thereof:

$$HOCH_2-(CHOH)_n-CH_2NR^1R^2,$$  I wherein $R^1$ and $R^2$ are independently selected from the group consisting of a hydrogen atom, an alkyl group, $C(O)R^3$, and $SO_2R^4$; $R^3$ and $R^4$ are independently selected from the group consisting of an alkyl group, an aryl group, and an aralkyl group; and n is an integer from about 2 to about 5.

The groups $R^1$ and $R^2$ are independently selected from the group consisting of a hydrogen atom, an alkyl group, $C(O)R^3$, and $SO_2R^4$. Each of $R^1$ and $R^2$ may be a hydrogen atom, each of $R^1$ and $R^2$ may be an alkyl group, each of $R^1$ and $R^2$ may be $C(O)R^3$, or each of $R^1$ and $R^2$ may be $SO_2R^4$. In some embodiments, $R^1$ may be a hydrogen atom and $R^2$ may be an alkyl group, $C(O)R^3$, or $SO2R^4$. In other embodiments, $R^1$ may be an alkyl group, and $R^2$ may be $C(O)R^3$, or $SO_2R^4$. In still other embodiments, $R^1$ may be $C(O)R^3$, and $R^2$ may be $SO_2R^4$. When either or both of $R^1$ and $R^2$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. When each of $R^1$ and $R^2$ comprises an alkyl group, $R^1$ and $R^2$ may comprise the same alkyl group, or $R^1$ and $R^2$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

The groups $R^3$ and $R^4$ are independently selected from the group consisting of an alkyl group, an aryl group, and an aralkyl group. When either or both of $R^3$ or $R^4$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. In compounds of Formula I or pharmaceutically acceptable salts thereof, when both $R^3$ and $R^4$ groups are present, and when each of $R^3$ and $R^4$ comprises an alkyl group, $R^3$ and $R^4$ may comprise the same alkyl group, or $R^3$ and $R^4$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

When either or both of $R^3$ or $R^4$ are an aryl group, the aryl group may comprise one arene ring or more than one arene ring. Arene rings may comprise up to six carbon atoms, up to eight carbon atoms, up to ten carbon atoms, up to twelve carbon atoms, up to fourteen carbon atoms, up to sixteen carbon atoms, or up to eighteen carbon atoms. Arene rings may comprise a heteroatom, for example, nitrogen, oxygen, or sulfur. If more than one arene ring is present, the arene rings may be fused together, or they may be joined by a chemical bond. In compounds of Formula I or pharmaceutically acceptable salts thereof, when both $R^3$ and $R^4$ groups are present, and when each of $R^3$ and $R^4$ comprises an aryl group, $R^3$ and $R^4$ may comprise the same aryl group, or $R^3$ and $R^4$ may comprise different aryl groups. Non-limiting examples of aryl groups include substituted and unsubstituted phenyl, 1-naphthyl, 2-naphthyl, 9-anthracenyl.

When either or both of $R^3$ or $R^4$ are an aralkyl group, the aralkyl group may comprise one arene ring or more than one arene ring. The aralkyl group may comprise up to six carbon atoms, up to eight carbon atoms, up to ten carbon atoms, up to twelve carbon atoms, up to fourteen carbon atoms, up to sixteen carbon atoms, up to eighteen carbon atoms, or up to twenty carbon atoms. If more than one arene ring is present in the aralkyl group, the arene rings may be fused together, or they may be joined by a chemical bond. Arene rings may comprise a heteroatom, for example, nitrogen, oxygen, or sulfur. In compounds of Formula I or pharmaceutically acceptable salts thereof, when both $R^3$ and $R^4$ groups are present, and when each of $R^3$ and $R^4$ comprises an aralkyl group, $R^3$ and $R^4$ may comprise the same aralkyl group, or $R^3$ and $R^4$ may comprise different aralkyl groups. Non-limiting examples of aralkyl groups include benzyl, 1-phenylethyl, 2-phenylethyl, 3-phenylpropyl, 2-naphthylethyl, and 9-anthracenylmethyl.

In Formula I, n is an integer from about 2 to about 5. In some embodiments, the dental composition comprises a compound of Formula I, or a pharmaceutically acceptable salt thereof, wherein n is an integer having a value of about 5, about 4, about 3, or about 2. In some embodiments, n is an integer having a value of 5, or 4, or 3, or 2. It is understood that the dental composition may comprise more than one compound of Formula I, or a pharmaceutically acceptable salt thereof, and that the compounds may be represented by Formula I with different integer values of n. In these embodiments, the average value of n of a composition may be a non-integer.

Pharmaceutically acceptable salts include ammonium salts. In some embodiments, the dental composition of the invention comprises an ammonium salt. An ammonium salt may be represented as the reaction product of an acid with an amine, or as the reaction product of an amine with an alkylating agent such as, for example, iodomethane, bromoethane, or benzyl bromide. An ammonium salt includes a protonated amine compound, for example a compound of Formula I in which a $NR^1R^2$ group, wherein $R^1$ and $R^2$ are independently selected from the group consisting of a hydrogen atom and an alkyl group, has been protonated with an inorganic acid or an organic acid. An ammonium salt includes an alkylated amine compound, for example a compound of Formula I in which a $NR^1R^2$ group, wherein $R^1$ and $R^2$ are independently selected from the group consisting of a hydrogen atom and an alkyl group, has been alkylated with an alkylating agent.

An ammonium salt comprises at least one counter ion that may be an inorganic anion, an organic anion, or a combination of anions. A combination of anions includes a combination of more than one inorganic anion, a combination of more than one organic anion, or a combination of an inorganic ion and an organic anion. Inorganic ions include, for example, halide (fluoride, chloride, bromide, and iodide), nitrate, sulfate, tetrafluroborate, and tetra(aryl)borates. Tetra(aryl)borates include compounds having the formula $Z_4B^-$, where Z is an aromatic group, for example a substituted or unsubstituted phenyl group. Examples of tetra(aryl)borates include, but are not limited to, tetraphenylborate, tetrakis(4-methylphenyl)borate, tetrakis(2-methylphenyl)borate, tetrakis(1,3,5-trimethylphenyl)borate, tetrakis(4-fluorophenyl)borate, tetrakis(pentafluorophenyl)borate, and tetrakis(4-trifluoromethylphenyl)borate. Organic anions include, for example, alkanoates (such as, for example, acetate, propionate, and butanoate), benzoate, fumarate, maleate, tartrate, ascorbate, benzenesulfonate, toluenesulfonate, and citrate. In some embodiments, the pharmaceutically acceptable salt is free of unsubstituted or substituted tropolone.

In certain implementations, an ammonium salt may be formed by protonation of a compound of Formula I, wherein $R^1$ and $R^2$ are independently selected from a hydrogen atom and an alkyl group, with an inorganic acid, an organic acid, or a combination of an inorganic acid and an organic acid. In another embodiment, an ammonium salt may be formed by alkylation of a compound of Formula I, wherein $R^1$ and $R^2$ are independently selected from a hydrogen atom and an alkyl group, with an alkylating agent. In yet another embodiment, an ammonium salt may be formed by an ion exchange or metathesis reaction with a previously formed ammonium salt.

In some embodiments, $R^1$ and $R^2$ are each a hydrogen atom. In some embodiments, pharmaceutically acceptable salts comprise ammonium halides. In certain embodiments, the dental composition comprises a compound of Formula II or a pharmaceutically acceptable salt thereof. In some embodiments, the salt comprises an ammonium halide. In a specific embodiment, the ammonium halide comprises an ammonium chloride.

II

In some embodiments, $R^1$ comprises an alkyl group and $R^2$ is $C(O)R^3$, where $R^3$ comprises an alkyl group. In certain embodiments, $R^1$ comprises an alkyl group having from about one to about four carbon atoms, and $R^3$ comprises an alkyl group having from about four to about sixteen carbon atoms. In some embodiments, $R^1$ comprises a methyl group, and $R^3$ comprises an alkyl group having seven, eight, or nine carbon atoms. In some embodiments, the dental composition comprises a compound of Formula III, Formula IV, or Formula V.

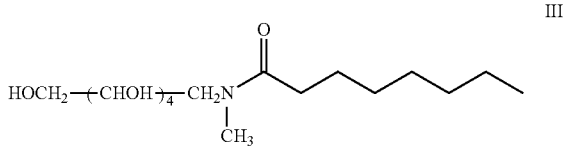

III

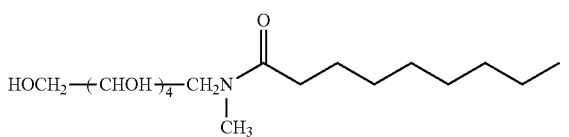

IV

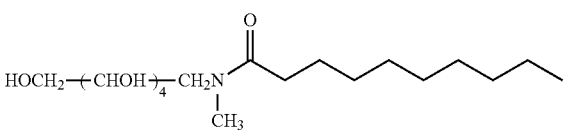

V

In some embodiments, $R^1$ is a hydrogen atom and $R^2$ comprises an alkyl group. In some embodiments pharmaceutically acceptable salts comprise ammonium halides. In some embodiments, the alkyl group comprises from about one to about eight carbon atoms. In certain embodiments, the dental composition comprises a compound of Formula VI or a pharmaceutically acceptable salt thereof. The salt may comprise an ammonium halide. In some embodiments, the ammonium halide comprises an ammonium chloride. In certain embodiments, the dental composition comprises a compound of Formula VII or a pharmaceutically acceptable salt thereof. The salt may comprise an ammonium halide. In some embodiments, the ammonium halide comprises an ammonium chloride. In some embodiments, $R^1$ and $R^2$ independently comprise an alkyl group having from about one to about eight carbon atoms. In certain embodiments, the dental composition comprises a compound of Formula VIII or a pharmaceutically acceptable salt thereof. The salt may comprise an ammonium halide. In some embodiments, the ammonium halide comprises an ammonium chloride.

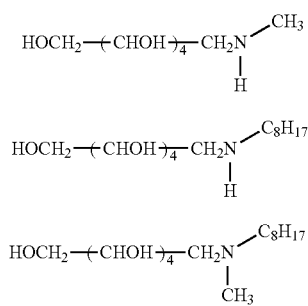

It is recognized that the compounds of Formulae I-VIII comprise chiral carbon atoms. For simplicity, in Formulae I-VIII the stereochemical configuration about each of the chiral carbon atoms is not specified. It is intended that Formula I-VIII, as used in this description and in the claims, represents each of the compounds having any of the possible stereochemical configurations. In some embodiments, the compounds of Formulae II though VIII are amino sugar alcohols and derivatives having the common names D-glucamine, N-methyl-N-octanoyl-D-glucamine, N-methyl-N-nonanoyl-D-glucamine, N-methyl-N-decanoyl-D-glucamine, N-methyl-D-glucamine, N-octyl-D-glucamine, and N-methyl-N-octyl-D-glucamine, respectively.

The dental composition may comprise an amount of a compound of Formula I, or a pharmaceutically acceptable salt thereof, sufficient to inhibit formation of a biofilm. In some embodiments, the dental composition may comprise an amount of a compound of Formula I sufficient to inhibit the formation of a biofilm in the oral cavity of a subject. In some embodiments, the dental composition may comprise an amount of a compound of Formula I sufficient to inhibit the formation of a biofilm on a hard surface in the oral cavity of a subject. In some embodiments, the hard surface may comprise a tooth. In some embodiments the dental composition may comprise an amount of a compound of Formula I sufficient to inhibit the formation of a biofilm on a dental restoration. The dental composition may contain up to about forty weight percent, up to about thirty weight percent, up to about twenty weight percent, up to about sixteen weight percent, up to about twelve weight percent, up to about ten weight percent, up to about six weight percent, up to about four weight percent, up to about two weight percent, or up to about one weight percent of a compound of Formula I, based on the combined weights of the compound, any binder, and any components such as a carrier or additives such as a flavoring agent or a coloring agent. The dental composition may comprise less than about ten weight percent, less than about five weight percent, less than about two weight percent, less than about one weight percent, less than about 0.6 weight percent, less than about 0.4 weight percent, less than about 0.2 weight percent, or less than about 0.1 weight percent of a compound of Formula I, based on the combined weights of the compound, any binder, and any components such as a carrier or additives such as a flavoring agent or a coloring agent.

In some embodiments, the dental composition may comprise a concentration of a compound of Formula I, or a pharmaceutically acceptable salt thereof, up to about 0.5 molar, up to about 0.3 molar, up to about 0.15 molar, up to about 0.1 molar, up to about 0.05 molar, up to about 0.03 molar, up to about 0.02 molar, or up to about 0.01 molar. In certain embodiments, the dental composition may comprise a concentration of a compound of Formula I, or a pharmaceutically acceptable salt thereof, up to about the solubility limit of the compound, or a pharmaceutically acceptable salt thereof, in a binder or in a pharmaceutically acceptable carrier. In other embodiments, the dental composition may comprise a concentration of a compound of Formula I, or a pharmaceutically acceptable salt thereof, greater than about the solubility limit of the compound, or a pharmaceutically acceptable salt thereof, in a binder or in a pharmaceutically acceptable carrier.

In some embodiments, the dental composition may provide a concentration of a compound of Formula I, or a pharmaceutically acceptable salt thereof, up to about the solubility limit of the compound, or a pharmaceutically acceptable salt thereof, in a medium such as, for example, water, culture broth, or saliva. In certain embodiments, the dental composition may provide a concentration of a compound of Formula I, or a pharmaceutically acceptable salt thereof, less than the solubility limit of the compound, or a pharmaceutically acceptable salt thereof, in a medium such as, for example, water, culture broth, or saliva. It is recognized that the solubility limit may be different in different media. As used herein, the term "provide a concentration" of a compound of Formula I, or a pharmaceutically acceptable salt thereof, refers to a property of the dental composition to release or transfer to a medium such as, for example, water, culture broth, or saliva an amount of a compound, or a salt thereof, resulting in a concentration of the compound, or a salt thereof, in the medium. In some embodiments, the dental composition may provide a concentration of a compound of Formula I, or a pharmaceutically acceptable salt thereof, up to about 0.5 molar, up to about 0.3 molar, up to about 0.15 molar, up to about 0.1 molar, up to about 0.05 molar, up to about 0.03 molar, up to about 0.02 molar, up to about 0.01 molar, up to about 0.005 molar, up to about 0.002 molar, or up to about 0.001 molar in a medium. In certain embodiments, the dental composition may provide a concentration of a compound of Formula I, or a pharmaceutically acceptable salt thereof, up to about the solubility limit of the compound, or a pharmaceutically acceptable salt thereof, in a medium.

The dental composition may be in contact with a surface in the oral cavity for a time sufficient to inhibit biofilm formation in the oral cavity. The time may be up to about one second, up to about five seconds, up to about ten seconds, up to about thirty seconds, up to about one minute, up to about two minutes, up to about five minutes, up to about ten minutes, up to about fifteen minutes, up to about thirty minutes, or up to about sixty minutes. The time may be less than about one month, less than about two weeks, less than about one week, less than about twenty-four hours, less than about twenty hours, less than about sixteen hours, less than about twelve hours, less than about ten hours, less than about eight hours, less than about six hours, less than about four hours, or less than about two hours.

The dental composition may comprise an amount of a compound of Formula I, or a pharmaceutically acceptable salt thereof, sufficient to inhibit formation of a biofilm comprising at least one species of bacteria found in the oral cavity of a subject. In some embodiments, the subject is a human. In other embodiments, the subject is a non-human animal. The bacteria include, for example, *Streptococcus mutans* and *S. sanguis*.

Binders

The dental composition of the invention typically comprises a binder. The binder may provide a reservoir of a composition comprising a compound of Formula I, or a pharmaceutically acceptable salt thereof, in an oral cavity of a subject. The composition may be released from the binder. The binder may hold a composition comprising a compound of Formula I, or a pharmaceutically acceptable salt thereof, on or near a surface in an oral cavity of a subject such that, for example, the surface may be exposed to the composition. The surface may be a hard surface, e.g., that comprises a tooth. The surface may be a dental restoration. The binder may comprise an addition polymer, a condensation polymer, or a combination of an addition polymer and a condensation polymer. In some embodiments, the binder comprises at least one of an acrylic polymer, an acrylamide polymer, a vinyl polymer, an epoxy polymer, a polyurea, a polyester, a polyanhydride, a polysiloxane, or a polyurethane. In certain embodiments, the binder comprises a film forming polymer.

In some embodiments, the binder comprises an acrylic polymer. Suitable acrylic polymers include polymers and copolymers of lower alkyl esters of acrylic or methacrylic acids. In this context, the term "lower alkyl" means a straight chain, cyclic, or branched alkyl group comprising about one to about eight carbon atoms. Examples of lower alkyl esters of acrylic or methacrylic acid include methyl acrylate, ethyl acrylate, propyl acrylate, butyl acrylate, isobutyl acrylate, tert-butyl acrylate, pentyl acrylate, neopentyl acrylate, hexyl acrylate, cyclohexyl acrylate, heptyl acrylate, cyclohexylmethyl acrylate, octyl acrylate, 2-ethylhexyl acrylate, isooctyl acrylate, methyl methacrylate, ethyl methacrylate, propyl methacrylate, butyl methacrylate, isobutyl methacrylate, tert-butyl methacrylate, pentyl methacrylate, neopentyl methacrylate, hexyl methacrylate, cyclohexyl methacrylate, heptyl methacrylate, cyclohexylmethyl methacrylate, octyl methacrylate, 2-ethylhexyl methacrylate, and isooctyl methacrylate.

Acrylic polymers may comprise at least one higher alkyl ester of acrylic or methacrylic acid. In this context, the term "higher alkyl" means a straight chain, cyclic, or branched alkyl group comprising more than about eight carbon atoms. Examples of higher alkyl esters of acrylic or methacrylic acid include decyl acrylate, dodecyl acrylate, tetradecyl acrylate, hexadecyl acrylate, octadecyl acrylate, behenyl acrylate, decyl methacrylate, dodecyl methacrylate, tetradecyl methacrylate, hexadecyl methacrylate, octadecyl methacrylate, and behenyl methacrylate.

Acrylic polymers may comprise at least one monomer having, for example, an acid group, a hydroxyl group, or an amino group. Non-limiting examples of such monomers include acrylic acid, methacrylic acid, 2-hydroxyethyl methacrylate, and 2-dimethylaminoethyl methacrylate.

Acrylic polymers may comprise at least one monomer having at least one ionic group. The ionic group may have a positive charge or a negative charge, or both a positive and a negative charge. Ionic groups include, for example, carboxylate groups, sulfonate groups, ammonium groups, and phosphonium groups.

Acrylic polymers may comprise at least one macromonomer. As used herein, the term "macromonomer" refers to an oligomer or a polymer comprising at least one polymerizable group. The macromonomer may be derived from, for example, methyl methacrylate or styrene. Exemplary macromonomers include methacrylate terminated poly(styrene) and poly(ethylene glycol) methyl ether methacrylate, available from Sigma-Aldrich Co., St. Louis, Mo. Acrylic polymers may comprise at least one silicone macromonomer, for example, a silicone macromonomer having dimethylsiloxane repeating units. Exemplary silicone macromonomers include vinyl terminated poly(dimethylsiloxane) and monoglycidyl ether terminated poly(dimethylsiloxane), available from Sigma-Aldrich Co., St. Louis, Mo.

Acrylic polymers may comprise at least one monomer comprising a fluorocarbon group. The fluorocarbon group may comprise a fluoroalkyl group, which may be a straight chain, branched or cyclic fluoroalkyl group. The fluorocarbon group may comprise a perfluoroalkyl group, which may be a straight chain, branched or cyclic perfluoroalkyl group. The fluorocarbon group may comprise a fluoroaryl group. The fluorocarbon group may comprise a perfluoroaryl group.

In some embodiments, the binder may comprise a reactive polymer. As used herein, the term "reactive polymer" refers to a polymer comprising at least one reactive group, i.e., a group that can react to form a covalent or ionic bond with a counterpart group on the same polymer chain, on another polymer chain (e.g., form a crosslink), on a different polymer, or on a surface. A surface may include a surface in the oral cavity of a subject, for example, a surface of a tooth. Examples of reactive groups include ionic groups, isocyanate groups, alkoxysilane groups, halosilane groups, acylsilane groups, ethylenically unsaturated groups (e.g., acrylate groups, methacrylate groups, and vinyl groups), epoxy groups, hydroxy groups, amino groups, ammonium groups, carboxy groups, carboxylate groups, azlactone groups, and anhydride groups.

In some embodiments, the binder may comprise a non-reactive polymer. As used herein, the term "non-reactive polymer" refers to a polymer that is substantially free of reactive groups, i.e., substantially free of groups that can react to form a covalent or ionic bond with counterpart groups on the same or another polymer chain or on a surface.

In some embodiments, the binder may comprise a hydrogel. The hydrogel may comprise a thermally responsive hydrogel, i.e., a hydrogel that undergoes a physical change in response to a change in temperature. Exemplary hydrogel binders are disclosed, for example, in U.S. Pat. No. 6,620,405 (Oxman et al.), U.S. Pat. No. 7,223,826 (Ali, et al.), and in U.S. Patent Publication No. 2004/0151691 (Oxman et al.).

Exemplary binders are disclosed in, for example, U.S. Pat. No. 5,130,347 (Mitra), U.S. Pat. No. 5,525,648 (Aasen et al.), U.S. Pat. No. 5,607,663 (Rozzi et al.), U.S. Pat. No. 5,662,887 (Rozzi et al.), U.S. Pat. No. 5,725,882 (Kumar et al.), U.S. Pat. No. 5,866,630 (Mitra et al.), U.S. Pat. No. 5,876,208 (Mitra et al.), U.S. Pat. No. 5,888,491 (Mitra et al.), U.S. Pat. No. 6,312,668 (Mitra et al.) and U.S. Patent Publication No. 2004/0185013 (Burgio et al.). In certain embodiments, the binder comprises a repeating unit that includes a fluoride releasing group. Fluoride releasing groups include tetrafluoroborate anions and are disclosed in, for example, U.S. Pat. No. 4,871,786 (Aasen et al.).

Exemplary polysiloxane binders are disclosed in, for example, U.S. Pat. No. 5,468,477 (Kumar et al.). In some embodiments, the polysiloxanes are dispersible in water. In certain embodiments, water-dispersible siloxane polymers include those functionalized with pendant moieties that include, for example, carboxylic acid groups, including dicarboxylic acid groups.

In some embodiments, the binder may be soluble in a pharmaceutically acceptable carrier or solvent. In some embodiments, the binder may be dispersible in a pharmaceutically acceptable carrier or solvent. In some embodiments, the binder may be a latex or emulsion, e.g., a latex or emulsion in which the carrier or the continuous phase comprises water. In certain embodiments, the latex or emulsion may comprise a self-emulsifying binder. In certain embodiments, the latex or emulsion may comprise a surfactant.

Pharmaceutically Acceptable Carrier

The dental composition of the invention may comprise a pharmaceutically acceptable carrier. The pharmaceutically acceptable carrier may comprise a liquid, a solid, or both. In some embodiments, the carrier may be a liquid at about room temperature. In other embodiments, the carrier may be a solid at about room temperature. In some embodiments, the carrier may be a liquid at about the temperature of the oral cavity of a human, i.e., at about 37° C. In other embodiments, the carrier may be a solid at about the temperature of the oral cavity of a human. Exemplary liquid carriers include water, alcohols (e.g., ethanol), glycerol, sorbitol, and liquid silicones. Exemplary solid carriers include polymers such as natural rubber, butyl rubber, poly(isobutylene), elastomers, styrene-butadiene rubber, polysaccharides, and waxes (e.g., beeswax).

Each non-carrier component of the dental composition may independently be dissolved, dispersed, suspended, or emulsified in the carrier. In some embodiments, at least one component of the dental composition is dissolved in the carrier. In some embodiments, at least one component of the dental composition is dispersed in the carrier. In some embodiments, at least one component of the dental composition is suspended in the carrier. In some embodiments, at least one component of the dental composition is emulsified in the carrier.

Additives

In some embodiments, the dental composition comprises a flavoring agent. In some embodiments, the flavoring agent includes an agent that imparts a flavor, e.g., a mint flavor, to the dental composition. In some embodiments, the flavoring agent includes an agent that imparts a tactile sensation, e.g., a cooling sensation, to the dental composition. The flavoring agent may be dissolved, dispersed, suspended, or emulsified in the dental composition. In some embodiments wherein the dental composition comprises a carrier, the flavoring agent may be dissolved, dispersed, suspended, or emulsified in the carrier.

In some embodiments, the dental composition comprises a coloring agent. The coloring agent can be any dye or pigment. The coloring agent may be dissolved, dispersed, suspended, or emulsified in the dental composition. In some embodiments wherein the dental composition comprises a carrier, the coloring agent may be dissolved, dispersed, suspended, or emulsified in the carrier.

In some embodiments, the dental composition further comprises an additive having a therapeutic property. The therapeutic property may include, for example, antiplaque activity, anticaries activity or antimicrobial activity. In some embodiments, the additive may be a pharmaceutically acceptable carrier such as, for example, ethanol. Examples of additives having anticaries activity include, for example, fluoride sources such as sodium fluoride and stannous flouride. Examples of additives having antimicrobial activity include glycerol esters of fatty acids (e.g., glyceryl monolaurate), salts of chlorhexidene (e.g., chlorhexidene gluconate), long chain alkyl ammonium or pyridinium salts (e.g., cetylpyridinium chloride), hydrogen peroxide, stannous fluoride, and triclosan. In some embodiments, the additive may have biofilm inhibiting or biofilm disrupting activity. The additive may be an enzyme (e.g., dextranase). The additive may be an essential oil. The additive may be a polymer. The additive may be a compound described in PCT Publication No. WO2009/014905.

The dental composition may have a form comprising a solution, a dispersion, a suspension, an emulsion, a solid, a paste, a foam, or a gel. Any component of the dental composition may be dissolved, dispersed, suspended, or emulsified in any other component of the dental composition. In some embodiments, the components are mutually soluble (i.e., miscible with each other).

The dental composition may be formulated by combining a compound of Formula I, or a pharmaceutically acceptable salt thereof, with at least one other component of the composition. The compound may be combined with a pharmaceutically acceptable carrier. If the carrier is a liquid, the compound may be dissolved, dispersed, suspended, or emulsified in the carrier. If the carrier is a solid, the compound may be combined with the carrier by, for example, milling or grinding. In one aspect, a compound of Formula I, or a pharmaceutically acceptable salt thereof, may be combined with other components of the composition after the other components have been combined with each other. In another aspect, all of the components, including a compound of Formula I, or a pharmaceutically acceptable salt thereof, may be combined at the same time.

Method and Kit

In another aspect, the invention provides a method of inhibiting biofilm formation on a surface of the oral cavity of a subject, comprising the steps of (1) providing a composition comprising a compound of Formula I or a pharmaceutically acceptable salt thereof, and (2) applying the composition to a surface in the oral cavity of a subject. The surface in the oral cavity of a subject includes, for example, a buccal surface, a gingival surface, a tooth, a dental restoration, and bone. The composition may be applied to the oral cavity of a subject by, for example, immersing, inserting, rinsing, spraying, brushing, swabbing, or combinations thereof. Spraying the composition may provide the composition in the form of, for example, an aerosol or a fine mist. The subject may be a human, or the subject may be a non-human animal. Non-human animals include mammals such as canines and felines.

In another aspect, the invention provides a kit comprising (1) a composition comprising a compound of Formula I or a pharmaceutically acceptable salt thereof, and (2) an application accessory. The application accessory can be a container, a sprayer, a brush, a swab, a tray, and combinations thereof. The application accessory can be any size. The kit may include more than one application accessory or more than one kind of application accessory (i.e., a sprayer and a brush). The kit may also comprise instructions for using the kit.

Features and advantages of this invention are further illustrated by the following examples, which are in no way intended to be limiting thereof. The particular materials and amounts thereof recited in these examples, as well as other conditions and details, should not be construed to unduly limit this invention.

EXAMPLES

Unless otherwise noted, all compounds and reagents were or can be obtained from Sigma-Aldrich Corp., St. Louis, Mo.

D-Glucamine was obtained from TCI America, Portland, Oreg.

N-Methyl-D-glucamine was obtained from MP Biomedicals, Solon, Ohio.

N-Methyl-N-octanoyl-D-glucamine was obtained from EMD Chemicals, Inc., San Diego, Calif.

N-Methyl-N-nonanoyl-D-glucamine was obtained from EMD Chemicals, Inc., San Diego, Calif.

N-Methyl-N-decanoyl-D-glucamine was obtained from EMD Chemicals, Inc., San Diego, Calif.

Quantitative Biofilm Inhibition Test

Compounds of the dental compositions of the invention, and comparative compounds, were evaluated for biofilm inhibition activity. Composite dental restorative (available under the trade designation "FILTEK SUPREME" from 3M ESPE Dental Products, St. Paul, Minn.) was placed in a 15 millimeter by 1 millimeter stainless steel die. The open ends of the die were then covered with polyester film and the die was subjected to a pressure of 68.95 MPa using a hydraulic press. While the die containing the composite restorative was under compression, the composite was irradiated for two minutes using a Model ACE light source (available from SCHOTT North America, Inc., Auburn, N.Y.). The discs of cured composite restorative were then further cured using a Model UniXS light box (available from Heraeus Kulzer, Inc., Armonk, N.Y.) for 1.5 minutes.

The cured discs of composite restorative were then immersed in ten milliliters of Streptococcus mutans culture (ATCC 25175; $10^6$ CFU/mL) prepared in brain heart infusion broth that contained 1.0 weight percent sucrose and 1 weight percent of a compound of the dental composition. The samples were incubated at 37° C. for approximately twenty hours, after which time the cured discs were removed from the broth and were gently rinsed with water. Each disc was placed in a separate test tube containing five milliliters of 1M aqueous sodium hydroxide solution, and each test tube was then sonicated for two minutes using a model SH1012-40-8 ultrasonic generator (manufactured by Branson Ultrasonics Corp., Danbury, Conn.) for two minutes to dislodge biofilm on the disc. The optical absorbance (optical density) of each aqueous sodium hydroxide solution was then measured at 550 nm using a Model ULTROSPEC III UV-visible spectrophotometer (manufactured by Pharmacia AB, Uppsala, Sweden). For each compound of the dental composition, five discs were separately incubated in broth and were evaluated separately to provide five optical density measurements. The average of the five optical density measurements was then calculated. Control or comparative samples, corresponding to each exemplary sample, were prepared essentially as described above except that the culture in brain heart infusion broth did not contain a compound of the dental composition. The average optical density of the control or comparative samples was determined as described above. The ratio, expressed as a percentage, of the average optical density for each compound sample to the average optical density for a control sample was calculated by dividing the average optical density for each compound sample by the average optical density for a control sample and multiplying the result by one hundred. The ratio was considered to be proportional to the average amount of biofilm on the five cured discs, i.e., relatively low average optical density ratio was considered to be indicative of inhibition of biofilm formation. The ratio for the control was 100%.

Qualitative Biofilm Inhibition Test

During the procedure for the Quantitative Biofilm Inhibition Test, each cured disc was visually examined after it was removed from the broth (and rinsed with water) and before it was placed in a test tube containing five milliliters of 1M aqueous sodium hydroxide solution. The presence or absence of visible biofilm on a disc was noted.

Bacterial Kill Rate Test

Compounds of the dental compositions of the invention were evaluated for extent of bacterial kill in culture. Overnight cultures of Streptococcus mutans in brain heart infusion broth ($10^6$ CFU/mL) was mixed with a 0.1 weight percent, 0.5 weight percent, or 1.0 weight percent aqueous solution of each compound of the dental composition. After a period of 2, 5, or 10 minutes, 1.0 mL of the mixture was transferred via pipette into a first tube containing 9.0 mL of Letheen broth to provide a $10^{-1}$ dilution. The contents of the tube were mixed using a vortex mixer. A 1.0 mL aliquot of this sample was transferred via pipette into a second tube containing 9.0mL of Letheen broth to provide a $10^{-2}$ dilution. A 0.1 mL aliquot of each dilution was plated and spread in duplicate on sheep blood agar in Petri dishes, using a "hockey stick" applicator, to provide $10^{-2}$ and $10^{-3}$ dilutions, respectively, on each plate. The plates were incubated at 37° C. for a period of 48 to 72 hours, and then the colony forming units were counted. The CFU counts were compared and the log reduction in the counts were calculated.

Minimum Inhibitory Concentration (MIC) Test

The MIC Test was carried out using successively lower concentrations of compounds. Sterile tryptic soy broth (50 microliters; TSB, available from BD Dfico, Becton, Dickinson and Company, Franklin Lakes, N.J.) was deposited into each well of a sterile polystyrene 96-well microtiter plate. Into each well in the first (leftmost) column of the plate, there was then deposited a 50 microliter aliquot (of known concentration) of a compound (i.e., a compound of Formula I, or a pharmaceutically acceptable salt thereof, or comparative compound). A 50 microliter aliquot of the mixture in the first (leftmost) well in the first row of the plate was transferred to the second well in the first row. A 50 microliter aliquot of the mixture in the second well in the first row was then transferred to the third well in the first row. The compound was successively diluted (1:1 dilution at each step) by transferring a 50 microliter aliquot from one well into the next well, across the row of the plate. This procedure was repeated for each row of the plate. Then, an overnight culture of Streptococcus mutans (strain ATCC 25175) was diluted 1:100 into sterile tryptic soy broth. A 50 microliter aliquot of the diluted S. mutans culture ($10^5$ CFU) was deposited into each well of the microtiter plate. The plate was then incubated at 37° C. for 24 hours in a sealed humidified chamber. The plate was then visually inspected to determine the lowest concentration of compound at which no bacterial growth was visible. This value was considered to be the minimum inhibitory concentration (MIC) for the compound. The test was repeated using Staphylococcus aureus (strain ATCC 6538) and Pseudomonas aeruginosa (strain ATCC 9027) in place of S. mutans.

Examples 1-5 and Comparative Example 1

Biofilm Inhibition

The Biofilm Inhibition Test was carried out using compounds of the dental composition. A control Test was carried out on a sample (Comparative Example 1) that did not contain an exemplary or comparative compound. In addition, a qualitative determination of biofilm formation was made for each Example and the Comparative Example in which each disc was visually examined before it was placed in the tube containing the aqueous sodium hydroxide solution. The data are given in Table 1. In Table 1, "OD Ratio" refers to the ratio, expressed as a percentage, of the average optical density for each compound sample to the average optical density for a control sample, calculated by dividing the average optical density for each compound by the average optical density for a control sample and multiplying the result by one hundred; "+" refers to a visual assessment that a compound inhibited biofilm formation, and "–" refers to a visual assessment that either a compound did not inhibit biofilm formation, or that bacteria grew in the culture broth.

TABLE 1

Biofilm Inhibition Data for Examples 1-5 and Comparative Example 1.

| Example | Compound | OD Ratio | Visual Assessment |
|---|---|---|---|
| 1 | N-Methyl-D-glucamine | 0% | + |
| 2 | N-Methyl-N-octanoyl-D-glucamine | 0% | + |
| 3 | N-Methyl-N-nonanoyl-D-glucamine | 0% | + |
| 4 | N-Methyl-N-decanoyl-D-glucamine | 0% | + |
| 5 | D-Glucamine | 101.5% | + |
| Comparative 1 | NONE (Control) | 100% | − |

Example 6

Concentration of Compound to Inhibit Biofilm Formation

The Biofilm Inhibition Test was carried out, using the compound of Formula VI, in broth containing 1.0, 2.5, or 5.0 weight percent sucrose. The data are given in Table 2. In Table 2, the millimolar concentration of compound that inhibited biofilm formation is given for each concentration of sucrose.

TABLE 2

Biofilm Inhibition Data for Example 6.

| | | Concentration of Compound to Inhibit Biofilm Formation | | |
|---|---|---|---|---|
| Example | Compound | 1 wt % Sucrose | 2.5 wt % Sucrose | 5 wt % Sucrose |
| 6 | N-Methyl-D-glucamine | 50 mM | 50 mM | 50 mM |

Examples 7-21

Minimum Inhibitory Concentration

A sample of each of the compounds of Formulae II, III, IV, V, and VI (0.050 g each) was dissolved in water (5 g). Each of the samples was evaluated using the Minimum Inhibitory Concentration (MIC) Test described above with *S. mutans*, *S. aureus*, and *P. aeruginosa*. The data are given in Table 3. In Table 3, "none" means that no inhibitory activity was detected.

TABLE 3

MIC Data for Examples 7-21.

| Example | Compound | Bacteria | MIC |
|---|---|---|---|
| 7 | D-Glucamine | S. mutans | none |
| 8 | N-Methyl-N-octanoyl-D-glucamine | S. mutans | none |
| 9 | N-Methyl-N-nonanoyl-D-glucamine | S. mutans | 2.50 mg/mL |
| 10 | N-Methyl-N-decanoyl-D-glucamine | S. mutans | 1.25 mg/mL |
| 11 | N-Methyl-D-glucamine | S. mutans | none |
| 12 | D-Glucamine | S. aureus | none |
| 13 | N-Methyl-N-octanoyl-D-glucamine | S. aureus | none |
| 14 | N-Methyl-N-nonanoyl-D-glucamine | S. aureus | none |
| 15 | N-Methyl-N-decanoyl-D-glucamine | S. aureus | 2.50 |
| 16 | N-Methyl-D-glucamine | S. aureus | none |
| 17 | D-Glucamine | P. aeruginosa | none |
| 18 | N-Methyl-N-octanoyl-D-glucamine | P. aeruginosa | none |
| 19 | N-Methyl-N-nonanoyl-D-glucamine | P. aeruginosa | none |
| 20 | N-Methyl-N-decanoyl-D-glucamine | P. aeruginosa | 2.50 mg/mL |
| 21 | N-Methyl-D-glucamine | P. aeruginosa | none |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of treating a surface in the oral cavity of a subject, the method comprising:
   (a) providing a dental composition comprising a compound of Formula I

$$HOCH_2-(CHOH)_n-CH_2NR^1R^2, \qquad I$$

wherein
   $R^1$ and $R^2$ are independently selected from the group consisting of a hydrogen atom, an alkyl group, and $C(O)R^3$, wherein at least one of $R^1$ and $R^2$ is $C(O)R^3$,
   $R^3$ is selected from the group consisting of an alkyl group having seven carbon atoms, an alkyl group having eight carbon atoms, and an alkyl group having nine carbon atoms, and
   n is an integer from about 2 to about 5; and
   (b) applying the dental composition to the surface in the oral cavity of the subject.

2. The method of claim 1, wherein the dental composition further comprises an additive with antimicrobial activity.

3. The method of claim 2, wherein the additive with antimicrobial activity is selected from the group consisting of glycerol esters of fatty acids, salts of chlorhexidine, long chain alkyl ammonium salts, long chain alkyl pyridinium salts, hydrogen peroxide, stannous fluoride and triclosan.

4. The method of claim 2, wherein the additive with antimicrobial activity is selected from the group consisting of glyceryl monolaurate, chlorhexidine gluconate and cetylpyridinium chloride.

5. The method of claim 1, wherein the dental composition further comprises chlorhexidine gluconate.

6. The method of claim 1, wherein $R^1$ is selected from a hydrogen atom and a methyl group, and $R^2$ is $C(O)R^3$.

7. The method of claim 1, wherein the dental composition is a film forming composition.

8. The method of claim 1, wherein the dental composition further comprises a binder.

9. The method of claim 8, wherein the binder comprises a film forming polymer.

10. The method of claim 8, wherein the binder comprises at least one of an addition polymer or a condensation polymer.

11. The method of claim 8, wherein the binder is selected from the group consisting of an acrylic polymer, a vinyl polymer, an epoxy polymer, a polyurea, a polyester, a polyanhydride, a polysiloxane, a polyurethane, and combinations thereof.

12. The method of claim 8, wherein the binder comprises an acrylic polymer.

13. The method of claim 1, wherein the dental composition further comprises a pharmaceutically acceptable carrier or solvent.

14. The method of claim 13, wherein the pharmaceutically acceptable carrier or solvent comprises ethanol.

15. The method of claim 13, wherein the pharmaceutically acceptable carrier or solvent is selected from the group consisting of water, alcohol, glycerol, or a combination thereof.

16. The method of claim 1, wherein the dental composition further comprises a flavoring agent, a coloring agent, or a combination thereof.

17. The method of claim 1, wherein the step of applying comprises immersing, inserting, rinsing, spraying, brushing, swabbing, or a combination thereof.

18. The method of claim 1, wherein the surface is a hard surface.

19. The method of claim 18, wherein the hard surface comprises a tooth.

20. A kit for treating a surface in the oral cavity of a subject, the kit comprising:

(a) a dental composition comprising a compound of Formula I

$$HOCH_2-(CHOH)_n-CH_2NR^1R^2, \qquad I$$

wherein
  $R^1$ and $R^2$ are independently selected from the group consisting of a hydrogen atom, an alkyl group, and $C(O)R^3$, wherein at least one of $R^1$ and $R^2$ is $C(O)R^3$,
  $R^3$ is selected from the group consisting of an alkyl group having seven carbon atoms, an alkyl group having eight carbon atoms, and an alkyl group having nine carbon atoms, and
  n is an integer from about 2 to about 5; and
(b) at least one applicator selected from the group consisting of a container, a sprayer, a brush, a swab, a tray, and combinations thereof.

21. The kit of claim 20, further comprising (c) instructions for applying the dental composition to a surface in the oral cavity of a subject using the at least one applicator.

* * * * *

UNITED STATES PATENT AND TRADEMARK OFFICE
CERTIFICATE OF CORRECTION

PATENT NO.          : 8,647,608 B2                                           Page 1 of 1
APPLICATION NO.     : 13/664452
DATED               : February 11, 2014
INVENTOR(S)         : Jie Yang It is certified that error appears in the above-identified patent and that said Letters Patent is hereby corrected as shown below:

On the Title Page, Item (56)

Page 2, Column 2 (Other Publications)
Line 1, Delete "Strptococcus" insert -- Streptococcus --, therefor.
Line 6, Delete "SStudies," insert -- Studies, --, therefor.
Line 39, Delete "Microbilolgy" insert -- Microbiology --, therefor.

In the Specification

Column 5
Line 48-49, Delete "tetrafluroborate," insert -- tetrafluoroborate, --, therefor.

Column 11
Line 56, Delete "flouride." insert -- fluoride. --, therefor.
Line 59, Delete "chlorhexidene" insert -- chlorhexidine --, therefor.
Line 59, Delete "chlorhexidene" insert -- chlorhexidine --, therefor.

Signed and Sealed this
Twenty-fourth Day of June, 2014

Michelle K. Lee
*Deputy Director of the United States Patent and Trademark Office*